Figure 1:
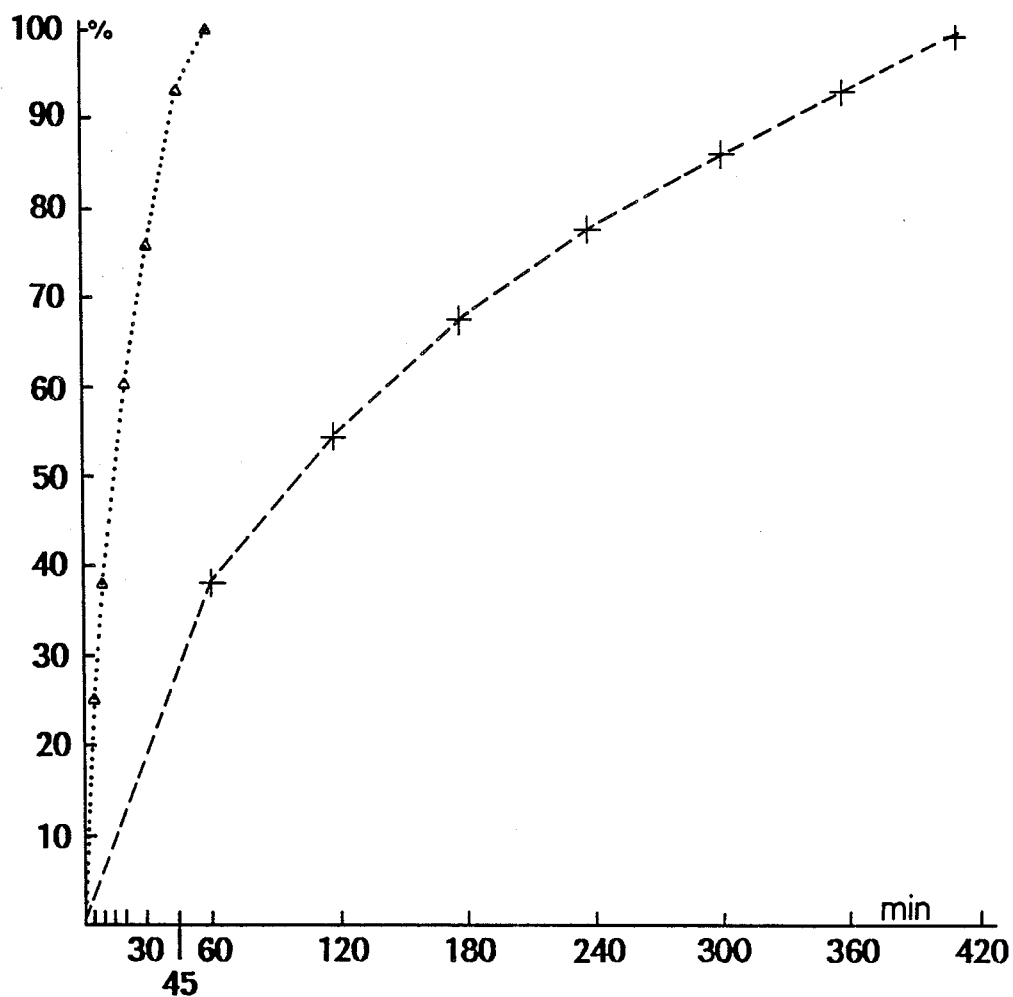

United States Patent [19]

Schäfer

[11] Patent Number: 4,895,873
[45] Date of Patent: Jan. 23, 1990

[54] CALCIUM SALT OF VALPROIC ACID

[75] Inventor: Helmut Schäfer, Kayhude, Fed. Rep. of Germany

[73] Assignee: Desitin Arzenimittel GmbH, Hamburg, Fed. Rep. of Germany

[21] Appl. No.: 169,058

[22] Filed: Mar. 16, 1988

[30] Foreign Application Priority Data

Mar. 20, 1987 [DE] Fed. Rep. of Germany ....... 3709230

[51] Int. Cl.$^4$ ..................... A61K 31/19; C07C 53/128
[52] U.S. Cl. ...................................... 514/557; 562/606
[58] Field of Search ......................... 562/606; 514/557

[56] References Cited

FOREIGN PATENT DOCUMENTS

| 2442M | 4/1964 | France ................................ 562/606 |
| 215531 | 11/1984 | German Democratic Rep. ..................................... 562/606 |
| 215533 | 11/1984 | German Democratic Rep. ..................................... 562/606 |
| 81/00562 | 3/1981 | PCT Int'l Appl. ................. 562/606 |

Primary Examiner—Vivian Garner
Attorney, Agent, or Firm—Nixon & Vanderhye

[57] ABSTRACT

The invention relates to a new crystalline calcium salt of valproic acid, in which per molecule 5 valproic acid radicals are associated with one calcium ion. The salt is non-hygroscopic and has superior galenic characteristics as active agent in pharmaceutical preparations, particularly for oral application.

The calcium salt is useful for the treatment of epilepsy and febrile convulsions.

5 Claims, 1 Drawing Sheet

CALCIUM SALT OF VALPROIC ACID

The invention relates to a novel calcium salt of valproic acid, containing per molecule 5 valproic acid radicals associated with one calcium ion, as well as to a process for the preparation thereof.

The pharmaceutical activity of valproic acid and its alkali metal and alkaline earth metal salts, particularly sodium salts is known. These compounds have proved particularly advantageous in treating special forms of epilepsy and febrile convulsions.

However, the galenic preparation of these compounds is difficult. Valproic acid is an oily liquid. Although the sodium salt is present as a crystalline solid, it is extremely hygroscopic and liquifies very rapidly. Therefore both compounds are only suitable to a limited extent for the preparation of oral administration forms.

Attempts have been made to overcome these difficulties by preparing more stable, non-hygroscopic alkali metal or alkaline earth metal salts of valproic acid. Thus, European patent 34 172 describes dimers of 1 molecule of valproic acid and 1 molecule of sodium valproate or ½ mole of calcium valproate. The salts are obtained in crystalline form. The corresponding calcium dihydrogen valproate has a melting point of 175° C.

European patent application 141 267 describes polymeric calcium salts of valproic acid, which comprise monomers, in which in each case 4 valproic acid radicals are associated with a calcium ion.

Finally, European patent application 143 271 describes metal salts of valproic acid, in which in each case 3 molecules of valproic acid are associated with a monovalent metal salt of valproic acid, namely the potassium, cesium or rubidium salt.

In the aforementioned, prior art alkali metal or alkaline earth metal salts of valproic acid, in each case the ratio of the alkali metal ion to the valproic acid or the valproate radical is 1:2 or 1:4.

According to the invention, surprisingly a calcium salt of valproic acid has been found, in which per molecule 5 valproic acid radicals are associated with one calcium ion. The inventive salt, hereinafter also called calcium pentavalproate, is obtainable in crystal form, the melting point of the crystals being 84° to 85° C. The crystals are not hygroscopic and are extremely stable. They dissolve very well in non-polar solvents, such as e.g. hexane and can always be recrystallized from the solution.

Examined microscopically, the substance is crystalline and uniform. Monocrystal examinations (optical and radiographic) give triclinic symmetry and the dimensions of the elementary cell. The morphology consists of the faces (100), (110), (010) and (001). For a probable density of 1.08, two formula units $Ca(C_8H_{15}O_2)_2 \cdot [C_8H_{16}O_2]_3$ can be calculated in the elementary cell.

The following hypothetical formula is assumed for the inventive calcium pentavalproate:

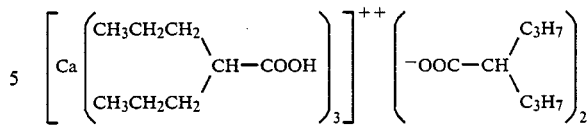

However, the invention is independent of the proof of the correctness of this formula.

The salt can be prepared in that calcium hydroxide and valproic acid are mixed together in a molar ratio of 1:5 in acetone. The mixture is refluxed until a substantially clear solution is formed. The solution is optionally filtered and after subsequent cooling colourless crystals with a melting point of 84° to 85° C. are obtained.

After grinding to a suitable particle size, the crystalline substance can optionally be processed with conventional carriers and additives to oral dosage forms, such as tablets or capsules.

The formulations prepared with the inventive active substance have modified release and resorption kinetics compared with known preparations (cf. FIG. 1).

The greatly delayed release of the active substance from the inventively prepared calcium pentavalproate products in artificial gastric juice (0.1% sodium hydrogen carbonate solution) in particular allows the conclusion to be drawn that there is a desirable, delayed resorption.

The invention is illustrated but not limited hereinafter by means of examples.

EXAMPLE 1

Preparation of calcium pentavalproate.

29.6 g of pulverized calcium hydroxide were stirred in a solution of 288.4 g of valproic acid in 1300 ml of acetone and the mixture was refluxed for 2 hours.

The almost clear solution was hot filtered. After cooling to −14° C, 206 g of the inventive calcium salt was removed by suction from the filtrate in the form of fine, colourless crystals. The melting point of the crystals was 84° to 85° C.

After concentrating to 1/5 of the volume, a further 68.6 g of crystalline salt was obtained from the mother liquor. The total yield was 274.6 g, corresponding to 91% of theory.

The mother liquor left behind after the second crystallization mainly contained valproic acid, which could be recycled for further use in the inventive process.

EXAMPLE 2

Preparation of tablets.

300 g of the inventively obtained calcium valproate were passed through a 0.5 mm sieve with 112 g of Avicel PH 102, 5 g of Aerosil R 972 and 3 g of calcium stearate and mixed in a Turbula mixer. By pressing out on an eccentric press, tablets were obtained whereby each tablet contained 300 mg of calcium pentavalproate.

EXAMPLE 3

Release of valproic acid from calcium pentavalproate tablets.

In each case two of the tablets obtained according to example 2 were placed in the small baskets of a dissolving tester. A 0.1% sodium hydrogen carbonate solution stirred at 150 r.p.m. was then allowed to act on the tablets at 37° C. and, starting after the first hour, at hourly intervals 1000 μl samples were removed from the bicarbonate solution. The active substance content in the samples was gas chromatographically determined as "valproic acid". The results are given in the following table.

| Removal Time | % Released, Based on 300 mg Total Active Substance Quantity |
| --- | --- |
| 1 h | 38 |
| 2 h | 55 |
| 3 h | 68 |
| 4 h | 78 |
| 5 h | 86 |
| 6 h | 93 |
| 7 h | 100 |

Under the same test conditions the release of the active substance from tablets was measured, which contained commercially available sodium valproate instead of the calcium pentavalproate according to the invention. Samples were taken after 5, 10, 15, 20, 30, 45 and 60 min. The release kinetics of the inventive calcium pentavalproate were compared with those of the commercially available product in FIG. 1.

I claim:

1. A calcium salt of valproic acid containing 3 moles of free valproic acid coordinated with calcium valproate and represented by the formula:

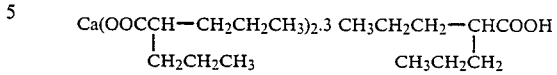

2. A pharmaceutical composition for the treatment of epilepsy or febrile convulsions containing a calcium salt of valproic acid containing 3 moles of free valproic acid coordinated with calcium valproate and represented by the formula:

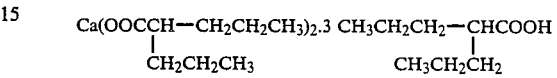

together with a pharmaceutically acceptable carrier.

3. The pharmaceutical composition of claim 2 in oral dosage form.

4. The pharmaceutical composition of claim 3 in the form of a tablet.

5. The pharmaceutical composition of claim 3 in the form of a capsule.

* * * * *